United States Patent [19]

Wilke et al.

[11] 4,048,214
[45] *Sept. 13, 1977

[54] PRODUCTION OF ALICYCLIC UNSATURATED COMPOUNDS HAVING PENDENT FUNCTIONAL GROUPS

[75] Inventors: Günther Wilke; Paul Heimbach, both of Mulheim (Ruhr), Germany

[73] Assignee: Studiengesellschaft Kohle m.b.H., Mulheim (Ruhr), Germany

[*] Notice: The portion of the term of this patent subsequent to June 22, 1993, has been disclaimed.

[21] Appl. No.: 605,367

[22] Filed: Aug. 15, 1975

Related U.S. Application Data

[60] Division of Ser. No. 250,533, May 5, 1972, Pat. No. 3,965,142, which is a continuation of Ser. No. 845,904, July 29, 1960, abandoned, which is a continuation-in-part of Ser. No. 582,775, Sept. 27, 1966, abandoned.

[30] Foreign Application Priority Data

Sept. 29, 1965 Germany ............................ 2443912

[51] Int. Cl.$^2$ ............................................. C07C 67/30
[52] U.S. Cl. ................................................... 560/128
[58] Field of Search ....................... 260/468 L, 514 L

[56] References Cited

U.S. PATENT DOCUMENTS

| | | | |
|---|---|---|---|
| 3,271,438 | 9/1966 | Connell | 260/464 |
| 3,271,468 | 9/1966 | Wilke et al. | 260/668 |
| 3,349,138 | 10/1967 | Larson et al. | 260/660 |
| 3,392,203 | 7/1968 | Olechowski et al. | 260/660 |
| 3,493,590 | 2/1970 | Chabarde | 260/410.9 |

OTHER PUBLICATIONS

Ruzicka et al., Helv. Chim. Acta 34, 401 (1951).

*Primary Examiner*—Robert Gerstl
*Attorney, Agent, or Firm*—Burgess, Dinklage & Sprung

[57] ABSTRACT

Cyclocooligomerization of at least one conjugated diene and an alkyl acrylate in the presence of a non-carbonyl containing, zero-valent nickel complex compound catalyst to form an olefinically unsaturated alicyclic ring compound having the non-hydrocarbon functional group pendent from the ring.

1 Claim, No Drawings

PRODUCTION OF ALICYCLIC UNSATURATED COMPOUNDS HAVING PENDENT FUNCTIONAL GROUPS

This application is a Divisional of application Ser. No. 250,533, filed May 5, 1972, now U.S. Pat. No. 3,965,142, which, in turn, is a continuation of Ser. No. 845,904, filed July 29, 1960, now abandoned, which, in turn, is a continuation-in-part of Ser. No. 582,775, filed Sept. 27, 1966, now abandoned.

In these parent applications, a process has been described for the catalytic dimerization and trimerization, respectively, of 1,3-diolefins, in which catalysts are used which are produced by mixing carbonyl-free compounds of nickel with organometallic compounds such as metal alkyls, metal aryls, or Grignard compounds, or with metal hydrides or with metal hydride complex compounds and electron donors. The electron donors used are Lewis bases such as cyclic ethers, tertiary amines, especially cyclic tertiary amines, alkyl or aryl phosphines, especially triphenylphosphine, or alkyl or aryl phosphites or compounds with a carbon-to-carbon multiple bond. Similar processes are claimed in German Auslegeschrift No. 1,126,864 of Badische Anilin- und Sodafabrik, wherein the catalysts are made by the reduction of transitional metal compounds by means of metals (Al, Mg), and German Auslegeschrift No. 1,144,268, wherein certain nickel-(0) compounds are used as catalysts. Furthermore, it is known that butadiene can be transformed with the aid of catalysts, such as $(R_3P)_2Ni(CO)_2$, into mixtures of cyclooctadiene-(1,5) and 4-vinylcyclohexene by the methods described in German Patent 881,511, and in U.S. Pat. No. 2,686,209.

According to Austrian Pat. No. 232,495, the catalytic cooligomerization of butadiene and ethylene, for example, results in the formation of cyclodecadiene-(1,5) compounds. According to all the processes described in the above-cited patents, substituted 1,3-dieolefins can be used instead of butadiene-(1,3).

It has now been found that it is possible to cyclocooligomerize at least one conjugated diene with an alkyl acrylate to form a 10 membered unsaturated alicyclic ring compound with a carboalkoxy pendent group thereon. It is surprising that the cyclocooligomerization proceeds very smoothly with very high conversions of the acrylic ester to the desired cyclic product with little or no attack on the carboalkoxy group and little or no conversion to open chain compounds. It is believed that this direction of the reaction is due to the particular catalyst being used. These cataylsts are per se known materials and are themselves the subject of other patents and patent applications of one or both of the inventors hereof. These catalysts are defined as non-carbonyl containing zero-valent nickel complex compounds. In particular, zero-valent nickel complexes of nickel with electron donors such as phosphines, phosphites, and multiple olefins are preferred. The reaction of this invention is schematically illustrated:

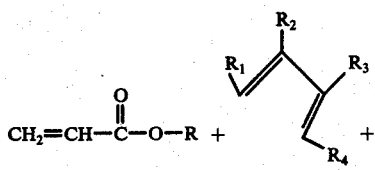

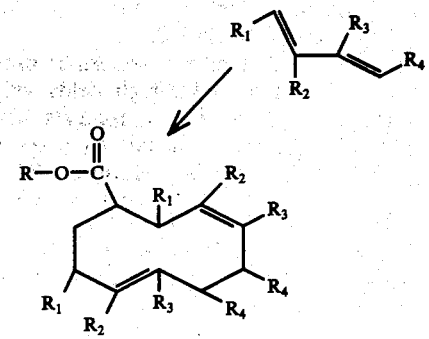

where R is an alkyl group, straight or branched chain, preferably having up to about 8 carbon atoms and wherein $R_1$, $R_2$, $R_3$, and $R_4$ are the same or different and may be hydrogen, alkyl, aryl, alkoxy, aryloxy, halo, haloalkyl, or the like. Alkyl, alkoxy, or haloalkyl groups suitably have up to about 8 carbon atoms in straight or branched chain configuration. Aryl or aryloxy groups suitably have one or two fused or unfused phenyl rings, preferably one, and may have one or several alkly and-/or halo substituents on one or more of the rings.

The selective cyclocooligomerization of this invention can be performed according to all the above-mentioned processes with the aid of catalysts of zero-valent nickel such as those described in German Auslegeschrift No. 1,140,569, and in Austrian Pat. No. 232,495. These catalysts are especially well suited to use in the cyclocooligomerization of this invention since with these cataylsts isomerization of the types which have been observed to a certain extent in the case, for example, of catalysts prepared by means of alkali metals according to German Auslegeschrift No. 1,126,864, does not occur. The carbonylfree, zero-valent nickel catalysts used in this invention have the additional advantage in the cyclocooligomerization process hereof in that they are cataytically active at lower temperatures than, for example, the catalysts which are prepared according to German Auslegeschrift No. 1,144,268. The complex compounds of zero-valent nickel described in German Auslegeschrift No. 1,191,375 can also be used as catalysts. In all cases in which substituted conjugated diene materials are used, the substituents themselves can be hydrocarbons or functional groups (e.g., alkoxy or carboxylic acid ester groups). They may also be hydrocarbons which contain such functional groups. The only functional groups involved are those which do not enter into any reactions with the catalysts, with the conjugated diene reactants, or with the unsaturated alicyclic products under the cyclocooligomerization reaction conditions.

The process according to the invention can be performed in the presence of inert solvents, but only those which attack neither reactants, nor products, nor the catalysts, nor the organometallic components, nor the metal hydrides which were used for the manufacture of the catalyst. Preferably, aliphatic or aromatic hydrocarbons, or aliphatic or cycloaliphatic ethers are used. It is particularly advantageous, however, to use the starting conjugated diolefins or the products that can be made according to the process as solvents in the manufacture of the catalyst, so that no foreign substances will have to be separated from the reaction product. The process can be performed at normal pressure or at elevated pressure. The pressure range in that case is determined by the desired direction of the reaction. The process can be performed at temperatures from −10° to 200° C, but preferably at 20° to 120° C.

Substituted 10 member rings can be produced by the process of the invention in high yields with reference to the acrylate reactant. The compounds that can be manufactured according to the invention are valuable starting products for further synthesis. The unsaturated cyclic products of this invention can be hydrogenated over palladium or Raney nickel catalysts to large ring saturated alcohols which are useful as solvents and as starting materials for dehydrogenation or oxidation to cyclic ketones which are valuable perfume intermediates. The unsaturated cyclic products can be oxidatively cleaved to form di and tri carboxylic acid products which are useful as polyester and polyamide polymerization intermediates.

The following are illustrative of the conjugated dienes which are useful in this invention: butadiene, isoprene, piperylene, chloroprene, ethyl butadiene, ethyl sorbate, phenylbutadiene, etc. The following are illustrative of the acrylates which are useful: methyl acrylate, ethyl acrylate, n-butyl acrylate, 2-ethyl hexyl acrylate, acrylonitrile, etc.

The acrylate monomer and the conjugated diene monomer are suitably admixed in mole ratios of about 1 : 10 to 10 : 1, preferably about 1 : 2, respectively. Where different conjugated dienes and different acrylates are cooligomerized, each member of the group should constitute at least about 20% of its group. It is preferred that where several members of each group are used each be employed in substantially equal proportions.

This invention will be illustrated by the following Examples:

EXAMPLE I

The catalyst was prepared by reducing 4.34 g = 17.05 mmoles of nickel acetyl acetonate and 9.19 g = 17.05 mmoles of tri-(0-phenyl phenyl)-phosphite in 85 cc of benzene, in which about 10 g of butadiene are dissolved, with 4.43 g = 34.1 mmoles of monoethoxy diethyl aluminum at 0° to 20° C. After the addition of 34 g of acrylic acid ethyl ester, approximately 25 g of butadiene were introduced at 60° C for 20 hours. After the customary distillation, the following is obtained after hydrogenation:

6.3 g = 2.1% ethylcyclohexene
233.8 g = 79.0% cyclooctane
17.8 g = 6.0% cyclodecanecarboxylic acid ethyl ester
2.7 g = 0.9% undecanic acid ethyl ester
35.3 g = 11.9% residue

EXAMPLE II

A solution of 4.64 g = 17.05 mm of Ni(cyclooctadiene-(1,5)$_2$ and 9.18 g = 1705 mm of tri-(o-phenylphenyl)-phosphite in benzene containing butadiene is used as the catalyst. For 10 hours, at 80° C, approximately 100 g of butadiene is added per hour, and at the same time, a total of about 50 g of acrylic acid ethyl ester is added drop by drop. After the customary distillation and hydrogenation, the following is obtained.

16.1 g = 1.9% ethylclohexane
740.0 g = 86.6% cyclooctane
77.1 g = 9.0% cyclodecanecarboxylic acid ester
4.1 g = 0.5% (cis-3,4- diethyl-cyclohexenyl)-carboxylic acid ethyl ester
9.3 g = 1.1% undecanic acid ethyl ester
8.2 g = 1.0% residue and higher oligomers

What is claimed is:

1. A process for preparing 3,7-cyclodecadiene carboxylic acid ethyl ester which comprises contacting butadiene and acrylic acid ethyl ester at a temperature of from about −10° to 200° C in the presence of a 0-valent nickel complex combined with tri-(ortho phenyl phenyl) phosphite as the sole electron donor, the mol ratio of butadiene to acrylic acid ethyl ester being at least 2:1, the reaction being carried out for a period of time sufficient to prepare said 3,7-cyclodecadiene carboxylic acid ethyl ester.

* * * * *

UNITED STATES PATENT AND TRADEMARK OFFICE
CERTIFICATE OF CORRECTION

PATENT NO. : 4,048,214
DATED : September 13, 1977
INVENTOR(S) : Günther Wilke et al It is certified that error appears in the above-identified patent and that said Letters Patent are hereby corrected as shown below:

Priority number "2443912" should read -- St 244391 --.
Title Page, Inventors, "Mulheim" should read -- Mülheim --.
Title Page, Assignee, "Mulheim" should read -- Mülheim --.
Column 1, line 39, "dieolefins" should read -- diolefins --.
Column 2, line 24, "alkly" should read -- alkyl --.
Column 2, line 37, "carbonylfree" should read -- carbonyl-free --.
Column 2, line 40, "cataytically" should read -- catalytically --.
Column 4, line 23, "ethylclohexane" should read -- ethylcyclohexane --.

Signed and Sealed this

Eleventh Day of April 1978

[SEAL]

Attest:

RUTH C. MASON
Attesting Officer

LUTRELLE F. PARKER
Acting Commissioner of Patents and Trademarks